United States Patent [19]

Francoeur

[11] Patent Number: 4,880,750

[45] Date of Patent: Nov. 14, 1989

[54] INDIVIDUAL-SPECIFIC ANTIBODY IDENTIFICATION METHODS

[75] Inventor: Ann-Michele Francoeur, San Diego, Calif.

[73] Assignee: Miragen, Inc., San Diego, Calif.

[21] Appl. No.: 71,707

[22] Filed: Jul. 9, 1987

[51] Int. Cl.[4] .................. G01N 33/548; G01N 33/561; G01N 33/566; G01N 33/577

[52] U.S. Cl. ...................................... 436/501; 283/70; 283/95; 435/7; 436/516; 436/518; 436/530; 436/543; 436/548; 436/809; 436/828

[58] Field of Search ...................... 283/70, 95; 422/56; 435/7, 805; 436/501, 513, 516, 518, 530, 543, 548, 809, 828

[56] References Cited

U.S. PATENT DOCUMENTS

| | | | |
|---|---|---|---|
| 2,445,586 | 7/1948 | Simons et al. | 117/1 |
| 3,964,992 | 6/1976 | Krotz | 204/299 R |
| 3,988,230 | 10/1976 | Krotz | 204/180 G |
| 4,031,197 | 6/1977 | Marinkovich | 436/513 |
| 4,136,229 | 1/1979 | Godet et al. | 428/537 |
| 4,452,901 | 6/1984 | Gordon et al. | 436/530 |
| 4,471,056 | 9/1984 | Grumet et al. | 436/513 |
| 4,582,788 | 4/1986 | Erlich | 435/6 |
| 4,582,789 | 4/1986 | Sheldon, III et al. | 435/6 |
| 4,591,570 | 5/1986 | Chang | 436/809 |
| 4,617,261 | 10/1986 | Sheldon, III et al. | 435/6 |
| 4,657,852 | 4/1987 | Grumet et al. | 435/7 |
| 4,708,931 | 11/1987 | Christian | 436/530 |
| 4,710,463 | 12/1987 | Murray | 435/68 |
| 4,713,349 | 12/1987 | Levin | 436/809 |

FOREIGN PATENT DOCUMENTS

| | | |
|---|---|---|
| 1215304 | 12/1986 | Canada . |
| 0135108 | 8/1984 | European Pat. Off. . |
| 0015702 | of 1897 | United Kingdom . |
| 2099578 | 12/1982 | United Kingdom . |
| 2135774A | 2/1984 | United Kingdom . |
| 2166445A | 10/1986 | United Kingdom . |
| 2166445B | 11/1987 | United Kingdom . |

OTHER PUBLICATIONS

"Leaving Holmes in the Dust", Newsweek, p. 81, (Oct. 26, 1987).

(List continued on next page.)

Primary Examiner—Robert J. Warden
Assistant Examiner—David A. Saunders
Attorney, Agent, or Firm—Workman, Nydegger & Jensen

[57] ABSTRACT

An identification method, applicable to the identification of animals or inanimate objects, is described. The method takes advantage of a hithertofore unknown set of individual-specific, or IS antibodies, that are part of the unique antibody repertoire present in animals, by reacting an effective amount of IS antibodies with a particular panel, or n-dimensional array (where n is typically one or two) consisting of an effective amount of many different antigens (typically greater than one thousand), to give antibody-antigen complexes. The profile or pattern formed by the antigen-antibody complexes, termed an antibody fingerprint, when revealed by an effective amount of an appropriate detector molecule, is uniquely representative of a particular individual. The method can similarly by used to distinguish genetically, or otherwise similar individuals, or their body parts containing IS antibodies.

Identification of inanimate objects, particularly security documents, is similarly affected by associating with the documents, an effective amount of a particular individual's IS antibodies, or conversely, a particular panel of antigens, and forming antibody-antigen complexes with a particular panel of antigens, or a particular individual's IS antibodies, respectively.

One embodiment of the instant identification method, termed the blocked fingerprint assay, has applications in the area of allergy testing, autoimmune diagnostics and therapeutics, and the detection of environmental antigens such as pathogens, chemicals, and toxins.

30 Claims, 8 Drawing Sheets

OTHER PUBLICATIONS

Wetton et al., "Demographic Study of a Wild House Sparrow Population by DNA Fingerprinting", Nature 327:147 (14 May 1987).

Nakamura et al., "Variable Number of Tandem Repeat Markers for Human Gene Mapping", Science 235:1616 (Mar. 27, 1987).

Francoeur et al., *J. Immunol.*, 136, 1648-1653, 1986.

Gill et al., "Forensic Application of DNA Fingerprints", Nature 318:577 (Dec. 12, 1985).

Jeffreys et al., "Positive Identification of an Immigration Test-Case Using Human DNA Fingerprints", Nature 317:813 (Oct. 31, 1985).

Jeffreys et al., "Individual-Specific Fingerprints of Human DNA", Nature 316:76 (Jul. 4, 1985).

Jeffreys et al., "Hypervariable 'Minisatellite' Regions in Human DNA", Nature 314:67 (7 Mar. 1985).

Wyman et al., "A Highly Polymorphic Locus in Human DNA", Proc. Natl. Acad. Sci. USA 77:6754 (Nov. 1980).

INDIVIDUAL-SPECIFIC ANTIBODY IDENTIFICATION METHODS

BACKGROUND OF THE INVENTION

The instant patent provides an identification method. It is premised on the formation of antigen-antibody reactivity profiles or antibody fingerprints, that can be used to uniquely identify animals and inanimate objects. The method is particularly valuable in the rapid identification of large numbers of individuals. One embodiment of the method, termed the blocked fingerprint assay, centers on detecting allergens, autoantigens, defined as "self antigens", and environmental agents such as pathogens, chemicals, or toxins, all of which substances possess the same epitopes, or antibody binding sites. Regarding the identification of inanimate objects, the method is particularly useful to identify security documents, and the like that have legal significance, as well as valuable art work. As applied to identifying animals, particularly humans, the instant method permits identification of individuals, and thus can be expected to be applied to the fields of forensic medicine, law enforcement, and immigration.

SECURITY DOCUMENT IDENTIFICATION

A new generation of photocopying, and photo offset machines has increased the potential for counterfeiting a wide variety of security documents. These machines are capable of producing near perfect replicas that are virtually indistinguishable from their authentic counterparts. Traditionally, security documents have been treated in generally one of two ways to discourage counterfeiters. The first method relies on the formation of a color associated with the original security document when attempts are made to undetermine its integrity. In involves impregnating into the document a small organic molecule which changes colors if the integrity of the document is tampered with. Examples of the latter are erasure marks, chemical treatment of the documents to remove valid signatures, etc. Chemicals that have been so employed are acid-base indicators such as phthaleins and sulphonephthaleins as described in U.S. Pat. No. 2,445,586 and in German Pat. No. 856,842. Unfortunately, however, these molecules are generally insoluble in water and, thus, are difficult to impregnate into documents without the use of organic solvents which in turn may adversely affect the document. Problems associated with the use of organic solvents lead to the development of water soluble indicators such as pyrene sulphonic acid as described in U.S. Pat. No. 4,136,229, which is soluble in aqueous solutions, and therefore, compatible with dispersion techniques used to impregnate a variety of security documents.

A second approach often used to ensure the authenticity of security documents, is to incorporate into the document materials which visually distinguish copies made of the original. Perhaps the best example of this approach is the use of security threads presently employed by a number of countries in their currencies. Other techniques involve incorporating holographic images so that unique visual images are apparent when documents are inspected with either visible, or ultraviolet light.

IDENTIFICATION OF INDIVIDUAL HUMANS

The three most common non-visual means for identifying people are blood typing, fingerprinting, and voice exemplars. Other methods include retinal scans and dental X-rays. Blood typing is based on the existence of groups of antigens present on blood cells. For example, the ABO system refers to four different groups of blood cell antigens: A, B, AB and O. The letters designate antigens present on the surface of red blood cells. Type A individuals have the A antigen; Type B individuals have the B antigen; Type AB have both antigens; and Type O has neither antigen. Thus, by analyzing a sample of a person's blood it is possible to identify him as to a particular blood group. It is, of course, immediately apparent that while this method may be used to identify one individual out of a small group of individuals, the method is limited when identification of an individual out of thousands of individuals is the goal. To do this, testing for many more blood group antigens is required and each test is a separate assay. Some newer tests make use of different isozymes that are present in body fluids, and suffer from the same limitations as do the blood typing tests. These methods can exclude certain individuals but can not differentiate between members of the same blood group.

Fingerprinting is perhaps a more accurate way of identifying an individual, and is widely used by virtually all law enforcement agencies around the world. It is based on the appearance of characteristic patterns of an individual's fingers, such as swirls, valleys and ridges. When the method is used, a statistical evaluation is given as to the degree of correspondence between known fingerprints obtained from the individual, and those fingerprints which are sought to be matched to the individual. The procedure is technically arduous, and often not definitive. For example, the way that fingerprints are catalogued allows room for ambiguities. Furthermore, in many instances of crime, fingerprints are not available.

The third procedure for identifying individuals is to match a voice recording with a voice exemplar of the individual. It is, of course, apparent that this method has little value in most instances, as there is seldom access to a recording of an individual's voice prior to the time that the match is sought.

A variety of immunological/biochemical tests based on genetics, are routinely employed in paternity testing, as well as for determining the compatibility of donors and recipients involved in transplant or transfusion procedures, and also sometimes as an aid in the identification of human and animals. While the instant method is of some use for paternity testing or organ or transfusion matching, it very importantly offers an identification method that is based on an alternate principle. Generally, the former procedures involve seriological testing for proteins encoded by the Human Leukocyte Antigen gene loci or, as it is more commonly known, HLA complex. Although a good deal of information is known concerning the genetic makeup of the HLA locus there are many drawbacks using HLA seriological typing as the means for identifying individuals in a large group. This is primarily because of the complexity of the serum used to do the testing, and the lack of widespread availability of standard serum necessary to conduct the test, especially when dealing with species other than mouse or man. However, the relatively recent advent of monoclonal antibody technology offers to bring considerable standardization to this field. Each of the HLA antigens must be tested for in a separate assay, and many such antigens must be identified in order to identify an individual, an arduous process when trying to identify one individual in a large group.

In addition to serological and mixed lymphocyte testing for the products of the HLA loci, more recent studies have identified DNA restriction fragment length polymorphisms (RFLP'S) indicative of different individuals, and these have been used in paternity testing, and transplant and transfusion compatibility testing. For example, Erlich, U.S. Pat. No. 4,582,788, has described a method for typing the HLA system based on the HLA DNA RFLP's. Further, Jeffreys et al. *Nature,* Volume 314, Page 67 (1985), have developed a powerful new identification system based on the analysis of repetitive DNA sequences (called "hypervariable minisatellite" regions) in human DNA. This method can also be applied to animals (see Wetton et al. *Nature,* Volume 327, Page 147 (1987)).

It will be appreciated by those skilled in the art that while the above methods are useful for identifying security documents, individuals, as well to perform paternity tests, and transplant and transfusion compatibility testing, that these methods are presently technically arduous, when used for the purpose of identifying individuals, are also time-consuming, and often necessitate the use of expensive laboratory equipment. Thus, it would be a significant contribution in the field if a single test could be developed for identification purposes, that is at least as powerful as those presently used, and that does not have many of their shortcomings, and that preferably is based on an entirely different principle. The systems that are based on DNA RFLP, or DNA "hypervariable minisatellite" regions, do not discriminate between genetically identical animals such as twins, and depend on the particular DNA probe used to discriminate between individuals that are closely related. The instant method, while influenced by the genetics of the individual in a general way, resembles most closely the forensic fingerprinting method in that it is the product of normal developmental processes that are unique for each individual, namely, that the immune system of each individual is highly variable when producing antibodies in response to antigens, and, in addition, the antibody genes are known to undergo a high degree of "somatic mutations" acting effectively as a "random number generator" leading to further diversity of the antibody repertoire (including the IS antibody repertoire). The instant method shares with the DNA fingerprinting method, the ability to discriminate between closely related individuals, and matching up newborns and mothers. It has the advantages of being able to discriminate between identical twins and is simple and rapid, especially when used with saliva or body fluids other than blood.

SUMMARY OF THE INVENTION

The instant invention, termed antibody fingerprinting, presents a general identification method whereby animate and inanimate objects can be identified. It is premised on the hithertofore unrealized discovery that humans, as well as animals generally have present in their body, a heretofore unknown set of individual-specific, or IS antibodies. When an individual's body fluid (or solids) containing IS antibodies, is screened against a panel (an n-dimensional array where n is typically 1 or 2), of multiple antigens (typically greater than 10,000 different antigens), distinct antigen-antibody complexes are formed. The antigen-antibody complexes are detected using an appropriate antibody-binding detector molecule, typically radioactive or enzymes that give a colored product on reaction with substrate. The antigen-antibody reactivity profile, or antibody fingerprint, can be used to identify individual humans or animals.

It is therefore an object of the instant invention to describe a simple immunological identification method that is applicable to people, and animals generally. The method is premised on the generation of an antibody mediated immune response. Saliva, tears, blood, serum, semen, urine, perspiration, lung washings, or other bodily fluid, or bodily solids such as tissue or feces, containing an organism's antibody repertoire is screened against a panel consisting of multiple different antigens, resulting in the formation of antibody-antigen complexes highly distinct of the organism from which the body fluid was obtained. All IS antibody isotypes are represented, thus allowing for the use of a wide range of detector molecules. The detector molecules used to detect the antigen-antibody complexes are widely available and include antibody binding proteins such as *Staphylococcus aureus* Protein A., or antibodies such as goat anti-human antibody or rheumatoid factor, or even cells with receptors for antibodies, such as lymphocytes. The detector molecules are appropriately labeled with tracer molecules, examples of such being enzymes, radioactive isotopes, magnetizable metals or photosensitive chemicals. The signals generated by the detector molecules on binding to the antigen-antibody complexes are then analyzed visually, or with appropriate instruments such as optical scanners or gamma radiation scanners. The profiles can be computer analyzed and stored for comparison at a later date with profiles from samples of unknown origin.

In addition to presenting a method for identifying people and animals, another object of the instant invention is to provide a method whereby severed bodily parts from people or animals can be identified. This situation might arise, for example, as a result of a catastrophic event such as a plane crash wherein bodily parts may be identified using IS specific antibodies.

It is a further object of the instant invention to describe a method whereby security documents can be identified by incorporating into, or associating with the document, IS antibodies obtained from one or more known individuals, that when tested with one or more panels of antigens, gives particular profiles of antigen-antibody reactivity, or antibody fingerprints. Security documents can also be identified by incorporating into, or associating with the document, a panel of multiple different antigens, that when screened with an effective amount of one or more particular sera containing IS antibodies, forms distinct antigen-antibody complexes, that when detected, generates an antigen-antibody reactivity profile, or antibody fingerprint.

It is yet another object of the instant invention to present an embodiment of the antibody fingerprint method, termed the blocked fingerprint assay. The method relies on competition by an effective concentration of IS antibody for epitopes present in a panel of multiple or primary antigens, with similar epitopes present in other antigenic or secondary molecules, usually in solution, and leads to inhibition or blocking of the formation of the antigen-antibody complexes on the panel on which is formed the antibody fingerprint, thus reducing the number of elements in the fingerprint. The blocking assay can be used, in a single assay, to detect many different secondary antigenic molecules with the same epitopes as are present on the primary antigens in the panel such as allergens, autoantigens, or environmental antigens such as infectious agents, chemicals, toxins, or synthetic peptides, as appropriate. This method also allows the identification of IS antibodies with anti-pathogen, anti-allergen, or autoantibody function. The IS antibodies thusly identified are useful in their own right in the construction of diagnostics for pathogens or allergens, therapeutics or diagnostics for autoimmune diseases.

An additional object of the instant invention is to provide kits that can be used to identify animals or security documents that consist of individual specific antibodies and accompanying reagents.

DETAILED DESCRIPTION OF THE INVENTION

The instant invention, antibody fingerprinting, provides a generally applicable identification method that is rapid and simple. It is premised on the finding that animals with an immune system react to the presence of foreign substances, or antigens, by mounting an immune response which involves the production of antibody molecules by lymphocyte cells. The antibody response is maintained over a multiyear period. I have found that during the early development (aged newborn to two years old) of each individual's immune system, an effective individual-specific antibody response (termed IS antibody response) is obtained, involving a large number of different antibody molecules. Consequently, IS antibodies present in the body fluids or solids of humans, or animals, can act effectively as an individual-specific "fingerprint" of that individual when screened against a suitable panel (n dimension array where n is usually one or two) containing multiple antigens. The effective number of antigens or epitopes (antibody-binding sites) that are present in the antigenic array is less than $10^{20}$ and typically greater greater than one thousand, depending on the level of statistical certainty desired in matching or discriminating between a few or a large number (greater than 100) of individual IS antibody "fingerprints." The antigen-antibody reactivity profile, when detected with an appropriate detector molecule, provides an individual-specific antibody fingerprint.

The instant identification method can be used to identify humans, or any organism that produces IS antibodies. Moreover, the method can be applied to distinguishing between or identifying inanimate objects such as blood transfusions, body parts, body excretions, or security documents. Further, it will be appreciated by those skilled in the art that elements of the antibody fingerprint may reveal much useful information about the immune status of an individual.

A unique feature of the instant identification method is that it is sensitive to persistent environmental antigens. In the blocked fingerprint assay, one embodiment of the instant method described at length below, the ability of secondary antigens is described such as environmental antigens, that compete with an effective amount of primary antigens in the panel for limited IS antibodies. Successful competition leads to a loss of antigen-antibody reactions with primary antigens in the panel, and subsequent loss of elements of the antibody fingerprint. Antibodies (including IS antibodies) that effectively cross-react with primary antigens in the panel, and with different secondary antigens can be used to identify immunologically similar primary and secondary antigens, such as environmental allergens, infectious agents, chemicals and toxins. The blocked fingerprint assay can also be used to detect persistent antigens that are natural or synthetic "autoantigens" that possess similar epitopes as do the primary antigens in the panel (autoantigens are defined as "self" antigens). Conversely, when the primary antigens in the panel consist of "self" or "autoantigens," or pathogens, the blocked fingerprint assay can be used to identify environmental antigens with similar epitopes as the autoantigens or pathogens, respectively. Some IS antibodies probably correspond to "autoantibodies" and on purification, may be useful in and of themselves, in the construction of diagnostics and therapeutics for autoimmune diseases.

Similarly, if the primary antigens correspond to pathogens in the environment, then the blocked fingerprint assay can be used to identify IS antibodies with anti-pathogen function. These IS antibodies may also be useful in the construction of anti-pathogen diagnostics or therapeutics, such as vaccines.

Thus it is readily apparent that this application of the method described herein has applications in the area of diagnostics and therapeutics for autoimmune diseases of man and animals.

The immunological method also may be used in conjunction with other identification methods based on different principles, such as traditional fingerprinting, or genetic tests such as HLA testing, DNA RFLP assays, or DNA fingerprint assays, and the several tests taken together, can be expected to provide a particularly accurate and powerful identification method, especially in situations involving a large number (more than a hundred) of individuals. The instant method has advantages of rapidity, simplicity, and cost effectiveness, especially when saliva is used, thus avoiding the problems of blood letting.

The basic immunological method, as applied to the identification of individuals includes:

(a) Obtaining an effective concentration of IS antibodies, preferably, in solution, from an individual's body fluid, such as urine, plasma, serum, saliva, perspiration, semen, or lung washings, or from an individual's body solids such as tissue or feces. The IS antibodies may be obtained in the dry state and as in the case of the body solids, resuspended into solution using a suitable buffer, such as isotonic saline. The effective concentration of each IS antibody specificity is less than 1 g/ml, preferably about 10 ng/ml-10 mg/ml.

(b) Reacting the antibody solution obtained in (a) with an effective panel of antigens where panel refers to an n-dimensional array of antigens, where n is typically one or two, to form antigen-antibody complexes. The panel of antigens contains multiple different antigens typically, but not necessarily, greater than ten thousand different antigens or epitopes and may be composed of natural antigens prepared from tissue cultured cells, or fresh animal tissue obtained from many different sources, or may consist of such extracts treated with enzymes or in other ways to generate fusion proteins or degradation fragments of different size, or may consist of purely synthetic polypeptides, or may consist of mixtures or subfractions of any of the above, so long as the antigens in the panel contain epitopes recognized by IS antibodies, and so long as the antigens are not contaminated with IS antibodies. The number of antigen-antibody complexes may be effectively increased or decreased by mixing the different kinds of antigens used in the panel. The effective concentration of each antigen in the panel is less than 1 g/mm$^2$, preferably 0.5 nanogram to 1 mg per square millimeter. The panel of antigens is formed by separating the antigens in n dimensions which is typically one or two, and can be effected by electrophoresis, isoelectric focusing, or other means;

(c) detecting the antigen-antibody complexes with an effective amount of an appropriate detector molecule.

The identity of an individual is established by comparing the resulting antigen-antibody reactivity profile, or antibody fingerprint, with that of an earlier obtained profile known to be characteristic of the individual. Similarly, individuals or inanimate objects, such as blood transfusions or tissues obtained after an air crash, may be distinguished by comparing antibody fingerprints obtained from each.

The method as applied to the identification of security documents includes:

(a) as above;

(b) associating an effective amount of characterized IS antibodies obtained from one or more individuals in (a) on or with the security document;

(c) reacting the IS antibodies associated on or with the security document with a particular panel of antigens;

(d) detecting the amount of antigen-antibody complexes with an effective amount of detector molecules.

The identity of the security document is realized by comparing the antibody fingerprint associated on or with the document with that of an earlier obtained fingerprint known to be characteristic of the antibodies. Similarly, an authentic document may be distinguished from a fraudulent document by comparing the antibody fingerprints associated with each. It should be appreciated that the method as applied to the identification of security documents can be the compliment of the above, that is:

(a) associating a particular panel of antigens on or with the security document;

(b) reacting the panel of antigens with an effective concentration of one or more particular individuals' characterized IS antibodies obtained from body fluids or solids of that individual(s);

(c) detecting antigen-antibody complexes with an effective concentration of an appropriate detector molecule.

A wide variety of assay techniques are available for detecting antigen-antibody complexes, commonly referred to as "immune complexes." It will be appreciated by those skilled in the art that the instant invention does not rely on an understanding of the molecular interaction of each particular antibody and antigen. All that is necessary is that a method be employed for detecting the immune complexes formed as a result of the individual-specific antibodies (IS antibodies) reacting with multiple antigens present in a panel, or n dimension array, where n is typically one or two.

A variety of immune complex assays are described in the *Methods of Enzymology*, Volume 73, Part B, Editor J. J. Langone and H. V. Vunakis, Academic Press. Immune complex assays described therein generally fall into two broad classes. In the first class are assays termed analyte excess/labeled antigen assays. Although these assays can be applied to realize the instant invention, they are tedious and time-consuming in that they are generally used to determine the presence of a single antigen. Since the instant method relies on a determination of the reactivity profile of multiple antibodies with multiple antigens, it will be appreciated that to obtain this information using analyte excess/labeled antigen assays would require considerable time wherein multiple different assays are performed for each antigen.

The second broad class of immune complex assays can be considered antigen/labeled antibody excess assays. Here, the antibody composition of normal sera is ascertained by screening the sera against a mixture of antigens generally bound to, and separated on, a solid surface. The antibody present in sera is in excess, and hence the phrase "excess antibody assay". The antigen mixture can be attached to a wide variety of solid surfaces, and then assayed by applying the sera. A second labeled antibody or antibody-binding molecule is applied which reveals the presence of antibody bound to the antigen present in the sera.

Typically, the antigenic material is separated in some way, most often by electrophoresis, to allow ready visualization of the reactivity profile of antibodies in the sera with multiple antigens. A wide variety materials has been used to construct solid support matrices that can be employed in these types of immune complex assays. Representative materials include polyacrylamide, and agarose. Additional, other materials including polystyrenes, polyvinylchloride, polyethylene, cellulose, and other natural or synthetic polymers may be employed.

A modification of the above-mentioned technique is the so-called immunoblotting procedure, also called Western blotting, described by Towbin et al. in Proceedings of the National Academy of Science, USA, Volume 76, Page 4350 (1979). This consists of separating an antigen mixture in one or two dimensions on a polyacrylamide gel, and then transferring the antigens from the gels onto a suitable surface, for example, nitrocellulose paper. The procedure generates a panel of antigens arrayed in one or two dimensions. The panel of antigens is then incubated with a blocking agent, for example a solution of bovine serum albumin, and detergents, such as Tween-20, to block or bind to sites on the panel that are not occupied by antigen. The panel is subsequently incubated with primary antibodies, washed to remove non-specifically bound antibodies, and then incubated with a detector molecule that recognizes the antigen-antibody complexes, typically through the antibody portion. The immunoblotting technique is advantageous in that it generally has lower backgrounds than other techniques, and further, it lends itself to a dipstick assay. The instant method is different from those previously described for the formation or detection of immune complexes because it involves individual-specific or IS antibodies.

The method of detecting antibody bound to antigen using a tracer-labeled antibody-binding molecule will differ depending on the nature of the substrate material to which the antigen is attached, the nature of the antigens themselves, and the nature of the antibodies involved. IS antibodies react in a typical fashion. Traditional methods utilize S. aureus Protein A or a labeled second antibody directed against the first antibody, wherein the label is most often radioactive, or an enzyme capable of hydrolyzing a substrate thereby producing detectable color. The color can be associated with fluid surrounding the matrix, or can be associated with the matrix itself. It will be appreciated by those versed in the art, that the second antibody itself will give an antibody fingerprint in the instant method, and is first preferably incubated extensively with the panel of antigens to adsorb out second antibody-specific IS antibodies present. The adsorbed second antibody may then be used as a detector molecule when combined with a suitable reporter molecule well known to those skilled in the art. By adsorbing the second anti-body to remove IS antibodies present, clear IS antibody fingerprint profiles are realized. Immunoblotting enables antibody binding to antigen to be detected by visualizing colored particulate precipitates and avoids the use of radioactive compounds. An effective concentration of antibodies present in immune complexes is typically 1 ng to 10 ug per complex per $mm^2$.

A number of enzymes can be coupled to protein A or second antibody, that form precipitates on a solid surface in the presence of a suitable substrate. A partial list includes horseradish peroxidase, glucose oxidase, and alkaline phosphatase.

In addition to enzymatically revealing the antigen-antibody complexes formed on a solid matrix, there exists non-enzymatic means of revealing the immuno complex. Many of these are well known to those skilled in the art, but perhaps particularly useful is the colloidal gold technique. The manner in which it is constructed and used with antibodies is described by De Mey et al in *Prot. Biol Fluids* (Editor Pepters), Paragon Press, Oxford, page 943 (1981), and Ami in *Immunochemistry: Applications and Pathology and Biology* (Editor Polak and Van Noorden) and Wright and Sons Ltd., London, page 83 (1983).

The preferred embodiment of the instant invention involves constructing a panel of one to ten thousand different antigens, using the immunoblotting procedure described by Towbin et al. Proceedings of the National Academy of Sciences, Volume 76, Page 4350 (1979).

The particular antigens used in the panel may vary, depending on the number of antigen-antibody reactions desired. For example, human HeLa cells contain approximately ten thousand different antigens, and can be prepared and separated electrophoretically according to molecular mass, using denaturing polyacrylamide gel electrophoresis systems, and subsequently electrophoretically transferred onto a matrix, such as nylon or nitrocellulose paper. The antigens are prepared according to appropriate protocols, for example, see Francoeur et al. Journal of Immunology, Volume 136, Page 1648 (1986). Unlike previously documented use of the immunoblotting technology, the instant invention is based on the formation and detection of immune complexes formed with individual-specific antibodies. A different individual-specific antibody fingerprint is obtained if a single individual's IS antibodies are reacted with total HeLa cell antigens, or partially degraded HeLa cell antigens. In both cases, the IS antibodies are likely the same, but the HeLa antigens are different in molecular mass and size. Thus, the antigens are located in different areas of the panel.

Individual specific antibodies are obtained from an individual's body fluids or solids, and reacted with the panel of antigens for a time sufficient for IS antibodies to bind antigen, typically for 30 minutes to an hour, but not more than three days. The IS antibodies are incubated neat (undiluted) or in an appropriate solution (e.g., isotonic saline) at a dilution of about less than one in $10^7$, preferably in the range of 1:10 or 1:20. The effective concentration of each antigen in the panel is less than 1 g/$mm^2$, preferably 0.5 nanogram to 1 mg per square millimeter. The nonspecifically bound antibodies are removed by washing, and the immune complexes detected by further incubation with an effective concentration of a labeled detector molecule such as $^{125}I$-Protein A, or with a labeled second antibody such as alkaline phosphatase-conjugated goat anti-human IgG, previously adsorbed to remove second antibody-specific IS antibodies reactive with the panel of antigens. The panel of antigens is washed to remove nonspecifically bound detector molecules, and an effective concentration of substrate material added if the second antibody carries an enzyme, resulting in the development of a colored product. If the detector molecule carries a radioactive tracer, X-ray film or other techniques can be used to detect the presence of the detector molecules by methods well known to those skilled in the art.

It will be appreciated by those skilled in the art that the IS antibodies present in a particular individual sera or other body fluids or solids, can be employed to identify or distinguish between inanimate objects, such as blood or body parts, or security documents. For the latter, a particular panel of antigens can be employed for this purpose as well, to be used to generate an antibody fingerprint with a particular individuals' IS antibodies. Such are generically referred to as security documents, by which is primarily meant any negotiable instrument which is convertible to cash, particularly currencies, checks, travelers checks, postal order, lottery tickets, trading checks, bearer bonds, and other financial documents. In addition, other documents which cover a different array of valuable rights are intended to come within the scope of the term security documents. Such would be passports, admission tickets, travel tickets and the like. Also, the instant method is applicable to determining the authenticity of labels attached to clothing, such as those which exhibit the trademark of a particular manufacturer.

The instant method may also be employed to ensure the authenticity of works of art, and the like. As applied to security documents the instant method involves associating with the item whose authenticity is sought to be determined, a record of the antibody-antigen reactivity profile. The preferred method is to associate with the security document an effective concentration of a particular individual's IS antibodies, for example, in the form of dried plasma on a filter paper inside of a sealed tube, and then, when the authenticity of the document is sought to be proved, react the antibodies with a particular panel of antigens and after detection of the immune complexes, observing the antigen-antibody reactivity profile, or antibody fingerprint, in comparison to a previously obtained fingerprint using the same IS antibodies. Alternatively, the particular panel of antigens may be associated with the documents and the fingerprint obtained with particular IS antibodies. In those instances where the antigens are small molecular weight molecules, this can be accomplished by impregnating the antigens directly into the document using the techniques as described in U.S. Pat. No. 4,037,007 and 4,136,226.

An additional approach is to chemically modify either the security document, the IS antibodies, the antigens, or both, so as to affect binding between the two, yet preserve the function of the molecules involved. One method for binding the panel of antigens whereby this can be accomplished is to chemically activate the security document, assuming the latter is composed at least partially of paper, or other similar chemically reactive substrate, by cyanogen bromide (CNBr) treatment. When CNBr activated paper is combined with proteinaceous antigens, the antigen binds irreversibly to the paper. The procedures for carrying out this reaction are well known in the art and are described by Eska in Methods of Enzymology, Volume 73, page 646, Editors Langone and Vunakis (1981). Additional reactions are available, and are well known to those skilled in the art.

When the identity of the security document is questioned, the IS antibodies, or the panel of antigens associated with it are reacted to form the immune complexes with the appropriate antibodies or panel of antigens respectively, and the immune complexes are detected with suitable detector molecules. In addition to the detector molecules described previously, additional labels attached to the antibody-binding molecule (i.e., protein A or adsorbed second antibody) can include fluorescent, bioluminescent, or chemiluminescent molecules as described in U.S. Pat. No. 4,478,817, or magnetizable, or radiation sensitive materials.

The following examples illustrate various aspects of the invention, but it will be obvious to those skilled in the art that various changes and modifications may be made therein without departing from the scope of the invention. For example, total antibodies, including the IS antibodies, from a particular individual may be labeled directly by reaction with detector molecules, and the detector-IS antibody complexes subsequently incubated with the panel of antigens, thus generating an antibody fingerprint. Another example, perhaps more properly called an antigen fingerprint, includes first separating the total antibodies, including IS antibodies (eg. by isoelectric focusing), and then reacting the antibodies with a mixture of labeled or unlabeled antigens, or a particular antigen detector molecule, and the immune complexes formed detected directly, or after reaction with a labeled detector molecule.

EXAMPLE I

"Antibody Fingerprinting" of Humans

An extract of human HeLa cells was prepared and used to form an antigenic panel as described in Francoeur et al. Journal of Immunology, Volume 136, Page 1648 (1986). HeLa cells were grown in standard laboratory tissue culture medium, isolated, lysed with a detergent, and centrifuged to remove any insoluble debris. The extract contained approximately ten thousand immunogenically different antigens, the bulk of which have not yet been antigenically defined. The material was subjected to electrophoresis on a sodium dodecyl sulfate polyacrylmide gel to separate the mixture according to molecular mass. The separated antigens present in the polyacrylamide gel were electrophoretically transferred onto Immobilon paper (obtained from Millipore Corporation) and the sites on the paper with no antigens bound were then blocked by incubation with a solution containing 4% instant powdered dry milk, using standard techniques. The paper was cut into strips approximately two millimeters in width. Each strip consists of a panel of some ten thousand different antigens arrayed in one dimension according to molecular mass. Separate panels of antigens were incubated with individual sera (containing IS antibodies), diluted 1:20 in the appropriate buffer, obtained from different individuals at different times, in this case, for three hours at room temperature, with constant agitation. The panels of antigens were washed, to remove unbound or nonspecifically bound antibodies, and incubated with $^{125}$I-Protein A for two hours. Following subsequent washing to remove unbound detector, the panels of antigens were dried and exposed to X-ray film for 4 hours at $-70°$ C. with an enhancer screen, and the film developed, according to established protocols.

Figure 1A:
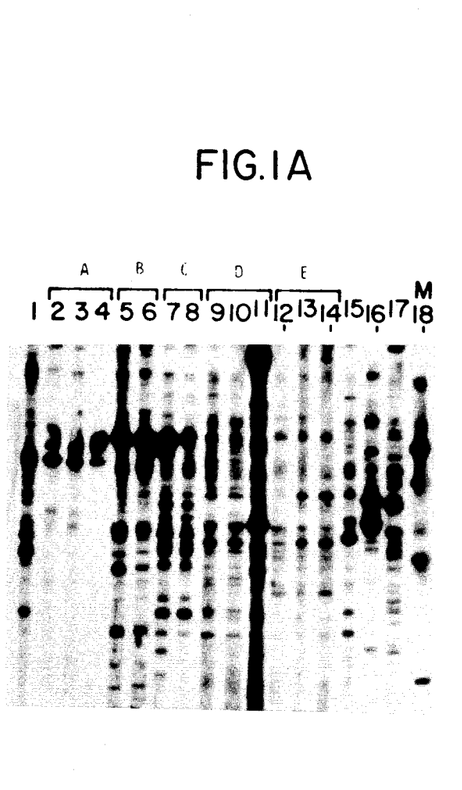
FIG. 1 shows the instant invention or antibody fingerprints obtained with individual human sera, including members of two families, over a period of years, and in one instance, when gravely ill. The sera were screened against a panel consisting of some ten thousand different human (HeLa cell) antigens and the antigen-antibody complexes were detected with $^{125}$I-labeled *S. aureus* Protein A that exposed Kodak X-AR film.
Figure 1B:
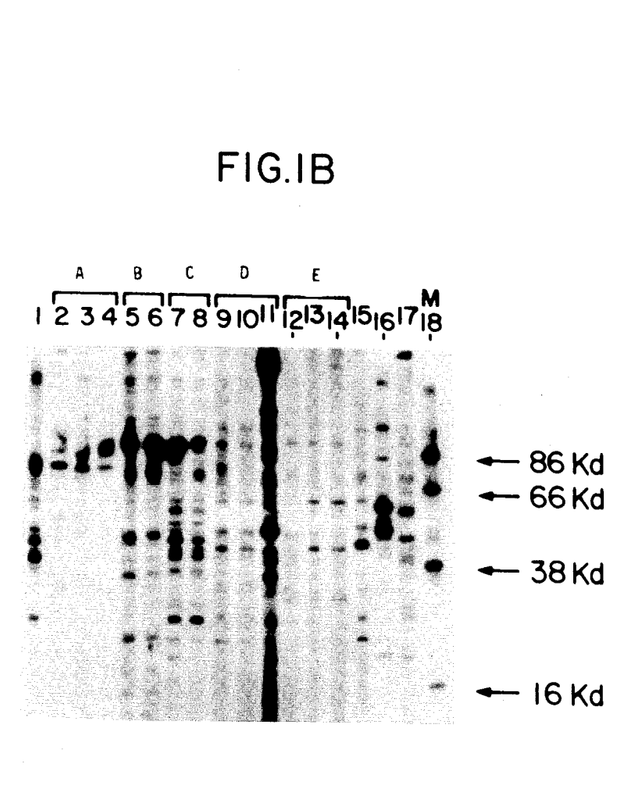

FIG. 1 shows two different exposures of the film; a long (3-day) and short (8-hour) exposure. The fingerprints are stable over a period of 4 years, 2 months for one individual (lanes 2–4); for 6 years, 7 months for a second individual (lanes 5 and 6); for 7 years for a third individual (lanes 7 and 8); for 7 years, 4 months for a fourth individual (lanes 9–11), and for 8 years, 3 months for a fifth individual (lanes 12–14). It is apparent that the fingerprints are virtually identical at early and late times, and are constant over a multiyear period. The individual whose fingerprints are shown in lanes 9 and 10 became gravely ill (vasculitis), and his fingerprint is obtained during this condition (lane 11). It is apparent that during the illness, the amount of antibody-antigen complexes was increased and thus the intensity of the fingerprint was stronger than when he was well. Minor changes in the fingerprint were detected. The second individual (lanes 5 and 6) is the daughter of the third individual (lanes 7 and 8). While the fingerprint of the mother and daughter are unique to those individuals, certain elements within the fingerprint appear to be common to both, suggesting that they share a common environment and/or genetic background that influences the immune response similarly. The fourth individual (lanes 9–11), is the son of the first individual (lanes 12–14), and again, while the fingerprints of the son and mother are unique to each individual, certain elements within the fingerprints are common to both. Lastly, lanes 1 and 15–17 show fingerprints of unrelated individuals while lane 18 shows the control fingerprint used for quality control. The molecular mass (Mr) of the antigens used in the panel is shown in kilodaltons (Kd).

EXAMPLE II

Figure 2:
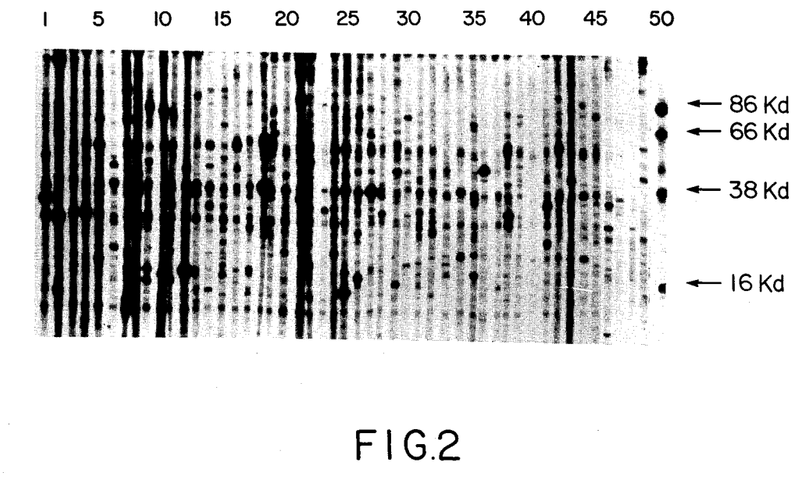
FIG. 2 shows the antibody fingerprints of individual normal humans ranging in age from newborn to ninety years old, using a HeLa cell panel of antigens.

Antibody-antigen Reactivity Profiles, or Antibody Fingerprints of Old and Young Normal Humans The method of the instant invention is applicable to both young and old humans. FIG. 2 shows the antibody fingerprints obtained from sera of normal individuals aged newborn to 90 years old. The panel of antigens and detector molecules used were the same as described in Example I. Approximately equal numbers of males and females are represented. An individual-specific profile was obtained in all cases. Some or all of the IS antibodies in newborns are likely transferred from the mother to the fetus as maternal antibodies in general are known to be passed to the fetus via the placenta, and are replaced by the child's own antibodies by approximately the sixth month after birth. The individual-specific (IS) antibodies appear to be fixed by approximately two years of age (see also examples IV and V). Lanes 1-7, 80-90 years; lane 8, 20 years; lanes 9-18, 70-79 years; lanes 19-28, 60-69 years; lanes 29-38, 50-59 years; lanes 39-42, 40-49 years; lanes 43-45, 30-39 years; lanes 46-49, Newborns. Lane 50 is a quality control fingerprint. The molecular mass (Mr) of the antigens in the panel is indicated.

EXAMPLE III

Figure 3:
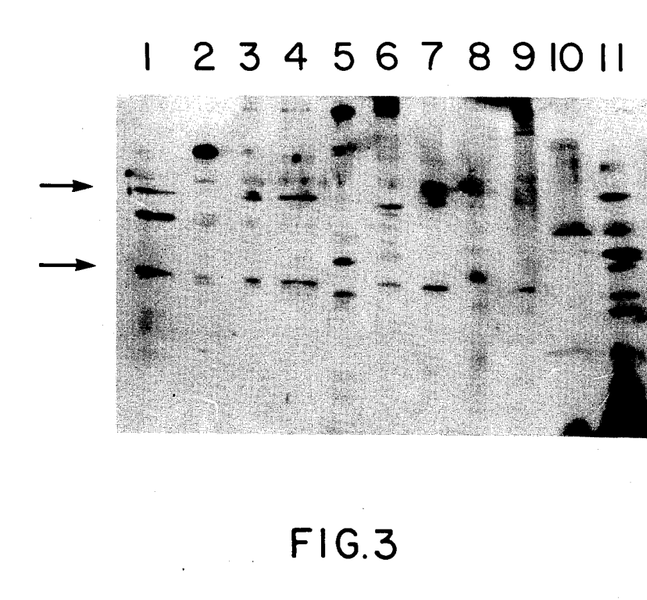
FIG. 3 shows antibody fingerprints obtained with an individual normal human serum screened against different panels containing multiple antigens prepared from various sources.

Antibody Fingerprints of a Single Normal Human Serum Obtained by Screening Against Different Panels of Antigens Normal human sera, or other body fluids containing IS antibodies, or similar fluids from other animals, can be screened against different panels of antigens prepared from complex antigenic mixtures. FIG. 3 presents antibody fingerprints obtained with a single normal human serum and reacted against panels of antigens prepared from human HeLa cells, a line of human cervical carcinomal cells that grow in the laboratory (lane 1); WIL-2 cells, a line of human B lymphocytes (lane 2); CV-1 monkey cells (lane 3); MDBK-cow cells (lane 4); dog muscle cells (lane 5); chicken embryo cells (lane 6); a mixture of different mouse cells lines (lane 7); frog oocytes (lane 8); Drosophila cells (lane 9); Bakers yeast (lane 10); RY1090 bacteria (lane 11). The detector molecule used was $^{125}$I-Protein A. It is apparent that the sera yields a different fingerprint with each antigenic panel tested. It is important to point out that this finding permits a large number of antigens to be employed, and, moreover, permits a cross check of the identity of the individual.

EXAMPLE IV

Antibody Fingerprints of Various Children, Aged Two Days to One Year

Figure 4:
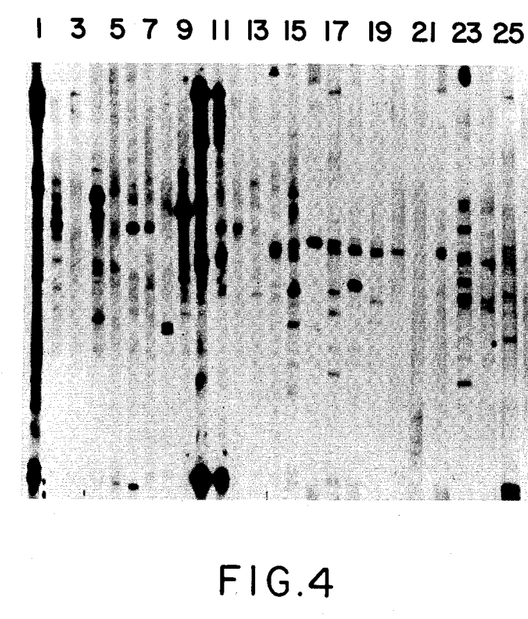
FIG. 4 shows the antibody fingerprints of individual normal and ill children aged one month to one year.

Sera were obtained from various male or female children, both normal and ill. The panel of antigens and detector molecule used were as described in Example I. Lanes 1-26: female, 12 months, normal; male, 10 days, normal; female, 12 months, ill; female, 8 months, ill; female, 7 months, ill; female, 1 month, normal; female, 10 months, normal; male, 12 months, normal; male, 4 months old, ill; male, 10 months, ill; male, 9 months, ill; male, 10 months, ill; male 3 months, ill; female 2 months, normal; male 9 months, normal; female, 2 days, normal; female, 5 months, ill; male 11 months, ill; male, 3 months, normal; male, 1 months, ill; male, 2 days, normal; male, 1 month, normal; female, 4 months, ill; male, 5 months, ill; male, 9 months, ill; female, 2 months, normal. It can be seen that the fingerprints of children less than a year old are generally simpler than older individuals, presumably because the immune system is in its early developing stages, and the full complement of IS antibodies is not yet established.

EXAMPLE V

Antibody Fingerprints of Various Children, Aged One Year to Six Year Old

Figure 5:
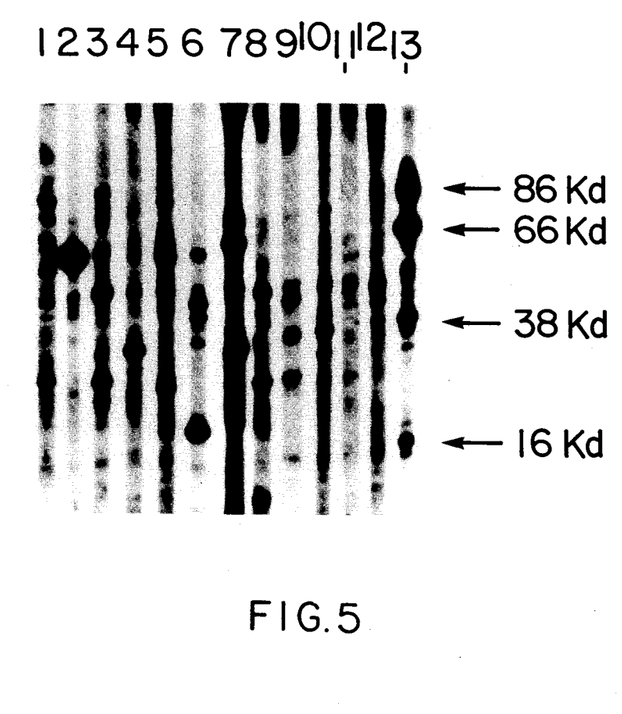
FIG. 5 shows the antibody fingerprints of individual normal and ill children aged one year to six years.

FIG. 5 shows that both normal and ill children of ages one to six years have IS antibodies that can be used to generate antibody fingerprints, similar to those of older individuals. The panel of antigens and detector molecules were as described in Example I. Lanes 1-12; female, 3 years, ill; male, 1 year, normal male, 2 years, ill; male, 4 years, ill; female, 5 years, ill; female, 6 years, ill; female 2 years, ill; male, 2 years, ill, female, 5 years, ill; male, 3 years, ill; female, 5 years, ill; male, 3 years, ill; male, 1 year, well; male, 1 year, ill. While it is clear from Example I that the antibody fingerprints are stable over a multiyear period, there is some indication that the fingerprints are altered by disease. The correlation with disease that we have found so far is that in some instances there is an increase in the amount of total antibody which presents a more intense fingerprint (see FIG. 1, lane 11, FIG. 5, lane 7. Lane 13, quality control fingerprint. The molecular mass of the antigens in the panel is indicated in kilodaltons.

EXAMPLE VI

Antibody Fingerprints of Animals

Figure 6:
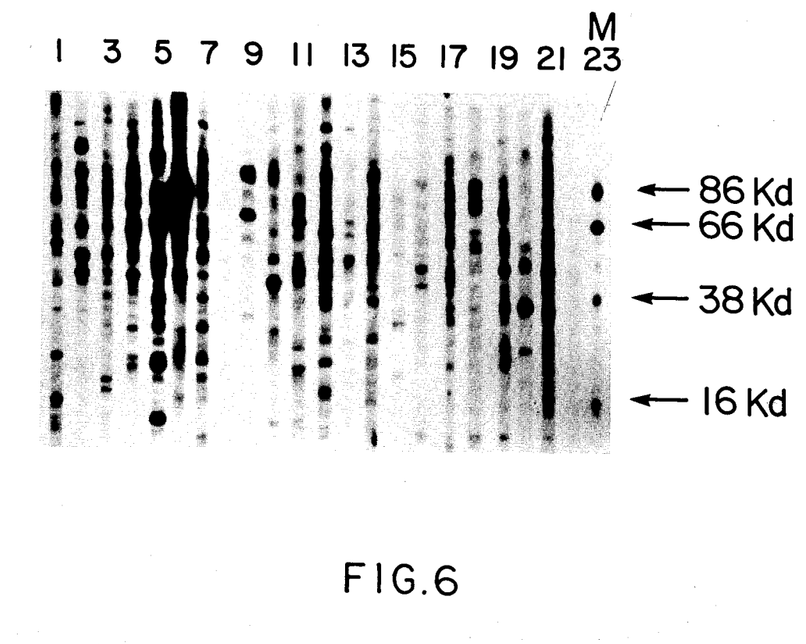
FIG. 6 shows the antibody fingerprints of individual normal and sick animals of different species and of different ages.

FIG. 6 shows antibody fingerprints of different animals. Sera was obtained from animals and tested against a panel of HeLa cell antigens. The detector molecule and antigens were as described in Example I. Lanes 1-3, 6, 15, 16, 19, 20, are sera from individual cats; lanes 4, 5, 7, 10-14, 17, 18, 21, are sera from individual dogs; lanes 8 and 9 are sera from individual monkeys; lane 22 is a horse serum; lane 23 is a quality control fingerprint. The various animals ranged from 2 months old to 18 years old and were approximately equally represented by both sexes. Most of the animals were well or had mild conditions, except for the cat and dog shown in lanes 5 and 6, which were gravely ill. FIG. 6 shows that antibody fingerprints may be obtained from different animals as well as from humans. The molecular mass (Mr) of the antigens in the panel is indicated in kilodaltons (Kd).

EXAMPLE VII

Antibody Fingerprints of Normal Human Families

Figure 7:
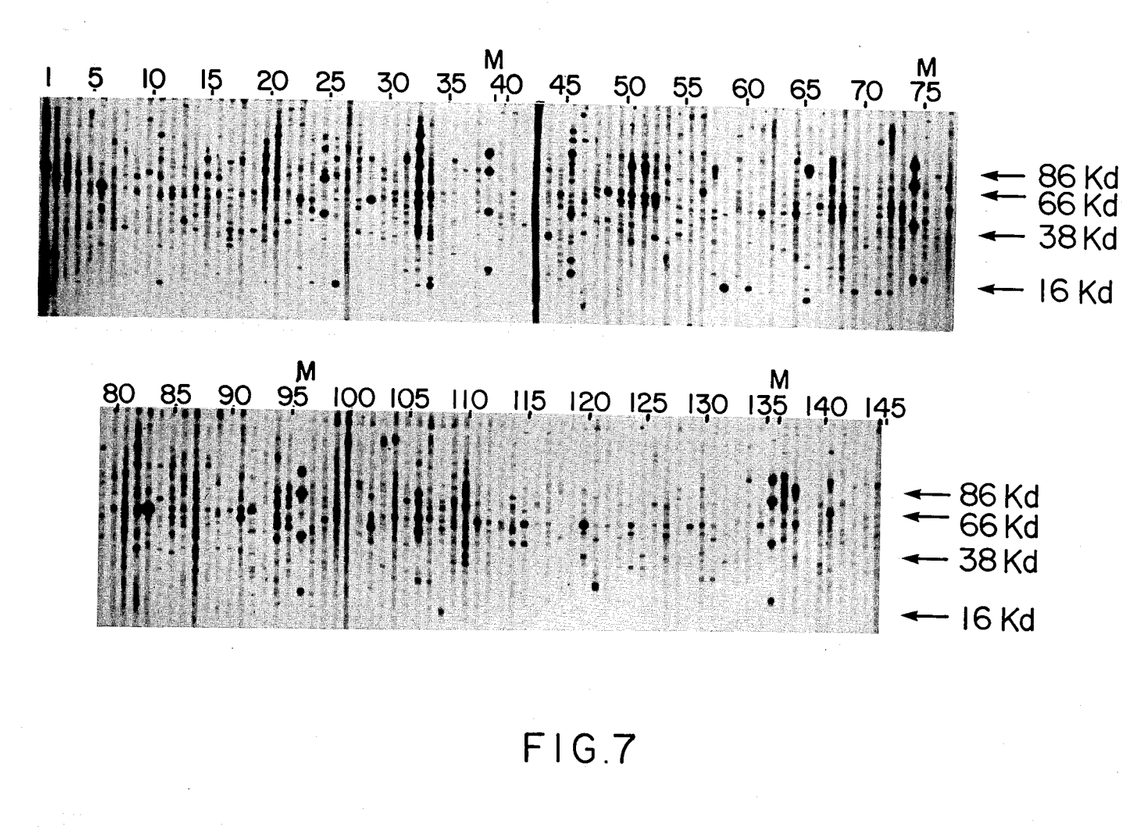
FIG. 7 shows the antibody profiles of individuals comprising different normal human families.

FIG. 7 shows antibody fingerprints of several normal human families. The children were all aged 12 years or older. The panel of antigens and detector molecules used were as described in Example I. Despite the genetic relatedness of the individuals in the families, each individual has a unique antibody fingerprint. In some cases, common "motifs" within the fingerprints can be discerned, which appear to be shared by members of a family, suggesting a common response to probably common environmental antigens. The fingerprints are marked off in sets of families with members of the families designated as F (father), M (mother), C (child). Quality control fingerprints are designated "M." The molecular mass of the antigens in the panel is indicated in kilodaltons.

EXAMPLE VIII

Figure 8:
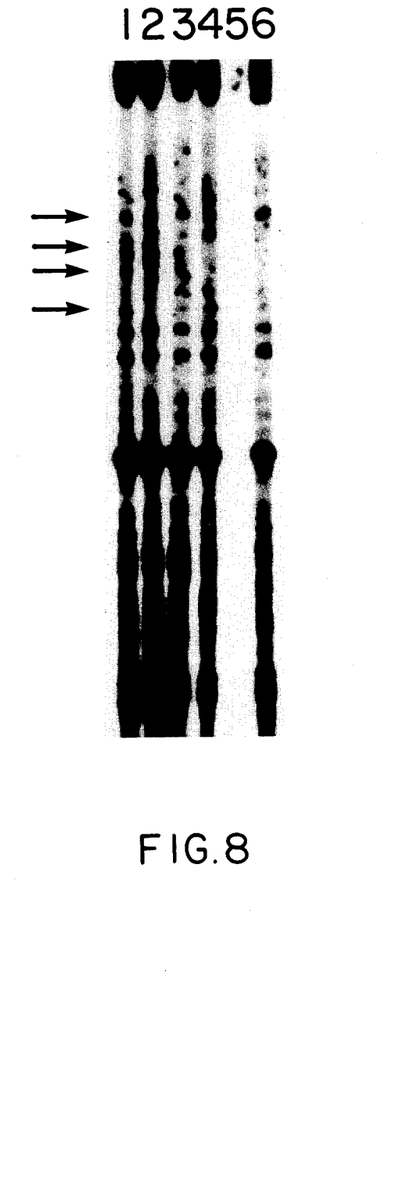
FIG. 8 shows the blocked fingerprint assay with secondary antigens in solution (obtained from different sources) used to compete with a panel of human HeLa cell primary antigens for IS antibodies present in an individual normal human serum.

The Blocked Fingerprint Assay as Used to Detect Environmental Antigens That Can Compete With Antigens in the Panel for IS Antibody Binding FIG. 8 shows the antibody fingerprints of a normal human individual, with or without the presence of competing secondary antigens. The X-ray film was purposely overexposed to show the fine details of the fingerprints. The panel of antigens consisted of separated human HeLa cell antigens, and the detector molecule was $^{125}$I-Protein A, as described in Example I. Different mixtures of antigens were incubated simultaneously with the IS antibodies and the panel of antigens at the same time for two hours. All fingerprints should be identical if no blocking occurs. Lane 1 shows no blocking agent, and it is apparent that there is no blocking of the fingerprint; lane 2, shows the results when human HeLa cell extract is used as the blocking agent. Two elements of the fingerprint are blocked arrows, bands 3 and 4), suggesting that one or more antigens present in the HeLa cell extract compete effectively with two HeLa antigens present in the panel for limiting IS antibodies; lanes 3 and 6 show the effect of blocking with bacterial extracts. Three elements of the fingerprint are blocked each instance (bands 2, 3 and 4. Lane 4 shows the results when yeast extract is used as the blocking agent. One element of the fingerprint is blocked (band 3). Lane 5 presents a control for the detector molecule in which the serum containing the IS antibodies was omitted. The control is blank indicating that the fingerprint results from binding of IS antibodies to antigens, and not as a result of nonantibody substances binding to the antigens in the panel.

There will be many modifications of the methods and compositions described above that are obvious to those of ordinary skill in the fields of immunology, immunochemistry, and genetic engineerng. Such modifications are intended to come within the scope of the invention.

I claim:

1. A method for identifying animals, comprising the steps of:
   isolating an effective amount of individual-specific antibodies from said animals;
   preparing a panel of multiple antigens separated in n dimensions on a solid surface, where n is one or two;
   forming a pattern of immune complexes of said antibodies and said antigens by contacting an effective amount of said antibodies to said panel of antigens for a time sufficient for said antibodies to bind to said antigens;
   revealing said pattern of immune complexes by contacting said immune complexes with an effective amount of detector antibody-binding molecules; and
   comparing the revealed pattern of immune complexes with a known pattern of immune complexes for the individual animal to be identified.

2. A method as described in claim 1 wherein said individual specific antibodies are isolated from materials selected from the group consisting of animal fluids and animal solids.

3. A method as described in claim 2 wherein said fluids are selected from the group consisting of animal sera, plasma, urine, saliva, semen, and lung washings.

4. A method as described in claim 2 wherein said animal solid is selected from the group consisting of feces, bodily tissues, and organs.

5. A method as described in claim 1 wherein said panel of multiple antigens is prepared from HeLa cells, and consists of about ten thousand different antigens.

6. A method as described in claim 1 wherein said panel of multiple antigens are selected from the group consisting of human cells, monkey cells, cow cells, dog cells, chicken cells, mouse cells, frog cells, fly cells, yeast cells, and bacteria cells.

7. A method as described in claim 1 wherein said detector molecules are selected from the group consisting of monoclonal antibody, polyclonal antibody, and Protein A.

8. A method as described in claim 7 wherein wherein said detector molecules are preabsorbed with said panel of antigens.

9. A method for identifying a security document, comprising the steps of:
   isolating individual-specific antibodies from an animal;
   associating said isolated antibodies on or with said security document;
   preparing a panel of multiple antigens separated in n dimension on a solid surface, where n is one or two;
   placing said isolated antibodies in a condition such that they can be contacted with said antigens to form immune complexes;
   forming immune complexes of said antibodies and said antigens by contacting an effective amount of said individual-specific antibodies to said panel of antigens for a time sufficient for said antibodies to bind to said antigens;
   revealing said immune complexes by contacting said complexes with an effective amount of detector antibody-binding molecules; and
   comparing the revealed pattern of immune complexes with a known pattern of immune complexes from said animal.

10. A method as described in claim 9 wherein said individual specific antibodies are isolated from materials selected from the group consisting of animal fluids and animal solids.

11. A method as described in claim 10 wherein said fluids are selected from the group consisting of animal sera, plasma, urine, saliva, semen, and lung fluid.

12. A method as described in claim 10 wherein said animal solid is selected from the group consisting of feces, bodily tissues, organs, and other bodily solids.

13. A method as described in claim 9 wherein said panel of multiple antigens is prepared from HeLa cells, and consists of about ten thousand different antigens.

14. A method as described in claim 9 wherein said antigens are selected from the group consisting of human cells, monkey cells, cow cells, dog cells, chicken cells, mouse cells, frog cells, fly cells, yeast cells, and bacteria cells.

15. A method as described in claim 9 wherein said detector molecules are selected from the group consisting of monoclonal antibody, polyclonal antibody, and Protein A.

16. A method as described in claim 9 wherein wherein said detector molecules are preabsorbed with said panel of antigens.

17. A method for identifying a security document as described in claim 9 wherein said isolated antibodies are incorporated on said security document.

18. A method of identifying a security document as defined in claim 9 wherein the step of isolating individual-specific antibodies from an animal comprises obtaining a quantity of body fluid or solids from said animal.

19. An identified security document, comprising:
a security document having associated therewith individual-specific antibodies.

20. A method for identifying a newborn and its mother, comprising the steps of:
isolating individual-specific antibodies from said mother and newborn;
preparing two panels of multiple antigens separated in n dimensions on a solid surface, where n is one or two;
forming a pattern of immune complexes of said mother's antibodies with said antigens by contacting an effective amount of said antibodies to one of said panels of antigens for a time sufficient for said antibodies to bind to said antigens;
forming a pattern of immune complexes of said newborn's antibodies with said antigens by contacting an effective amount of said antibodies to one of said panels of antigens for a time sufficient for said antibodies to bind to said antigens;
revealing said patterns of immune complexes by contacting said immune complexes with an effective amount of detector antibody-binding molecules; and
comparing said patterns of immune complexes of said mother and said newborn.

21. A method as described in claim 20, wherein said individual specific antibodies are isolated from materials selected from the group consisting of animal fluids and animal solids.

22. A method as described in claim 21 wherein said fluids are selected from the group consisting of animal sera, plasma, urine, saliva, semen, and lung washings.

23. A method as described in claim 21 wherein said animal solid is selected from the group consisting of feces, bodily tissues, and organs.

24. A method as described in claim 20 wherein said panels of multiple antigens are prepared from HeLa cells, and consists of about ten thousand different antigens.

25. A method as described in claim 20 wherein said panels of multiple antigens are selected from the group consisting of human cells, monkey cells, cow cells, dog cells, chicken cells, mouse cells, frog cells, fly cells, yeast cells, and bacteria cells.

26. A method as described in claim 20 wherein said detector molecules are selected from the group consisting of monoclonal antibody, polyclonal antibody, and Protein A.

27. A method as described in claim 26 wherein wherein said detector molecules are preabsorbed with said panel of antigens.

28. A method for identifying an animal comprising the steps of:
(a) isolating the individual set of antibodies from an individual animal to be identified;
(b) preparing a panel of multiple antigens obtained from animal cells, said panel being separated in n dimensions;
(c) contacting an effective quantity of the individual's antibodies to said panel of multiple antigens such that a pattern of a plurality of antigen-antibody complexes is formed;
(d) revealing said pattern of antigen-antibody complexes; and
(e) comparing the revealed pattern of antigen-antibody complexes formed with a known pattern of antigen-antibody complexes for the animal to be identified.

29. A method for identifying an animal as defined in claim 28 wherein said panel of antigens is prepared from HeLa cells.

30. A method for identifying an animal as defined in claim 28 wherein said panel of antigens is prepared from animal cells.

* * * * *